US006679986B1

(12) United States Patent
Da Silva et al.

(10) Patent No.: US 6,679,986 B1
(45) Date of Patent: Jan. 20, 2004

(54) CATALYTIC SUPPORT WITH AN OXIDE BASE FROM A METAL BELONGING TO THE SVI GROUP OF THE PERIODIC TABLE, ITS PREPARATION AND ITS USES

(75) Inventors: Pedro Da Silva, Le Havre (FR); Marc Bisson, Gainnevill (FR); Alain Milan, Fontaine la Mallet (FR); Sebastien Decker, Notre Dame de Gravenchon (FR); Joeri Denayer, Sint-Martens Lennik (BE)

(73) Assignee: Total Raffinage Distribution S.A., Puteaux (FR)

( * ) Notice: Subject to any disclaimer, the term of this patent is extended or adjusted under 35 U.S.C. 154(b) by 0 days.

(21) Appl. No.: 09/571,894

(22) Filed: May 16, 2000

(30) Foreign Application Priority Data

May 18, 1999 (FR) .............................. 99 06283

(51) Int. Cl.[7] ..................... B01J 21/06; B01J 37/03; B01J 27/053; C07C 5/27; C01G 49/02
(52) U.S. Cl. ................. 208/213; 208/254 H; 208/143; 208/108; 585/266; 585/446; 585/467; 585/520; 585/671; 585/709; 585/734; 585/940; 502/321; 502/325; 502/305; 502/337; 502/339; 502/349; 502/242
(58) Field of Search ............................... 502/339, 242, 502/439, 349, 325, 337, 321, 305; 208/213, 254 H, 143, 108; 585/671, 734, 446, 467, 709, 520, 266, 940

(56) References Cited

U.S. PATENT DOCUMENTS

| 3,793,041 | A | * | 2/1974 | Sowman ...................... 501/103 |
| 4,810,680 | A | * | 3/1989 | Bickford et al. ............. 501/103 |
| 5,075,277 | A | * | 12/1991 | Saiai et al. .................. 502/333 |
| 5,130,109 | A | * | 7/1992 | Wan ........................ 423/213.2 |
| 5,217,938 | A | * | 6/1993 | Reinalda et al. ............. 502/325 |
| 6,200,542 | B1 | * | 3/2001 | Poles et al. .................. 423/210 |

FOREIGN PATENT DOCUMENTS

| EP | 0 174 836 A2 | 3/1986 |
| EP | 0 520 543 A1 | 12/1992 |
| EP | 0 644 158 A1 | 3/1995 |
| WO | WO 97 18892 | 5/1997 |

* cited by examiner

*Primary Examiner*—Ngoc-Yen Nguyen
(74) *Attorney, Agent, or Firm*—Sughrue Mion, PLLC

(57) ABSTRACT

A catalytic support includes a substantial quantity of at least one SVI group Periodic Table metal oxide in which is incorporated silica. The mass ratio between the quantity of SVI group metal oxide and the quantity of silica it contains ranges between 5 and 70, the SVI group metal oxide is in crystalline form, and the specific surface of the support is greater than or equal to 160 $m^2/g$.

37 Claims, No Drawings

US 6,679,986 B1

CATALYTIC SUPPORT WITH AN OXIDE BASE FROM A METAL BELONGING TO THE SVI GROUP OF THE PERIODIC TABLE, ITS PREPARATION AND ITS USES

BACKGROUND OF THE INVENTION

This invention relates to a catalytic support particularly appropriate for the manufacture of catalysts for the treatment of hydrocarbons, and comprises in particular at least one oxide of a metal from the SVI group of the Periodic Table of the Elements, in which is incorporated a small quantity of silica. The invention also comprises preferred methods for the preparation of such a support. Lastly, the invention comprises catalysts prepared from such a support, as well as the uses of these catalysts in reactions for the treatment of hydrocarbons, such as, for example, hydrodesulphurization, hydrodenitrogenation, hydrogenation, hydroisomerization reactions etc.

It is well known that the oil industry resorts to many procedures whose object is to selectively transform certain compounds that are present in the oil cuts in order to obtain products whose properties are suitable for the sought use. These procedures usually call for one or more solid catalysts which must be specifically adapted to the chemical transformation we wish to complete and to the requirements tied to the implementation of the procedure.

Many of these reactions are done in the presence of a somewhat significant quantity of hydrogen. This is the case, for example, in the hydrodesulphurization and hydrodenitrogenation reactions that are aimed at eliminating the undesirable compounds, sulphuretted and nitrogenated hydrocarbons respectively, from the oil cuts. It is also the case in reactions that take place in the isomerization procedure of paraffins, which applies essentially to high-gravity gasolines, whose octane number is higher.

In most of these procedures for the treatment of oil cuts, the catalysts traditionally used today consist essentially of a high porosity alumina support, on which is deposited an active phase that corresponds to the active sites of the catalyst. This active phase often consists of a function that favors the transfers of hydrogen (in particular a group VIII metal of the Periodic Table of the Elements), usually combined with another compound, specific to the sought activity, namely the reaction to be catalyzed.

However, in general, the activity of the traditional catalysts is now proving to be insufficient, taking into consideration the increasing requirements as far as performance of the industrial procedures are concerned. For example, nowadays it is essential to increase the efficiency of the hydrodesulphurization procedures in response to stricter and stricter environmental standards concerning the maximum content of sulphuretted compounds in fuels.

This is why many researches have been undertaken in order to develop new, more active catalysts that would make it possible to meet these objectives without having to significantly modify the existing units, which would then make it possible to avoid costly investments.

It is well known that the nature and properties of the support have a significant influence on the activity of a catalyst, and among other things the researchers have tired to replace the traditional alumina based supports with new supports, capable of conferring a greater activity on the catalysts. In particular, the oxides of the SVI group metals of the Periodic Table of the Elements, such as zirconia for example, quickly proved to be relatively interesting potential candidates.

As early as 1970, U.S. Pat. No. 3,686,095 mentions the theoretical possibility of replacing the alumina with zirconia or magnesia. However, this patent limits itself to describing a hydrodesulphurization catalyst consisting of an active phase (hydrogenating metal combined with a group VI metal) deposited on a support with a very high porosity consisting of an alumina mixed with silica, meaning a completely traditional type of alumina base catalyst. If it mentions, in a theoretical manner, the possible use of alternative oxides, it in no way describes how to effectively prepare supports consisting of such oxides that have enough porosity to serve as a base for the preparation of industrial catalysts.

Indeed, if the zirconia type oxides do have interesting properties, to date they have not proved to be very appropriate for the manufacture of supports of industrial catalysts, to the extent that obtaining an adequate porosity is the result of the loss of specific properties brought on by these oxides. Therefore, many attempts have been made to try and improve supports with bases of such oxides in order to turn them into catalytic supports that can be used in the industry.

Thus, U.S. Pat. No. 5,021,385 proposes a catalyst that consists of a support with a high porosity made of co-precipitated zirconia and titanium oxide, on which are deposited molybdenum oxide (2 to 30% by weight) and nickel or cobalt oxide (1 to 10% by weight) and possibly phosphorus.

The FR patent number 2,661,171 describes a synthesis procedure of a stabilized zirconia with a high specific surface, designed to serve as a support for a hydrotreating catalyst. The high porosity of this catalyst is obtained thanks to the impregnation, before the calcination, of the amorphous zirconia by a solution of a stabilizing element chosen from among yttrium, nickel, aluminum, titanium, and phosphorus.

U.S. Pat. No. 5,262,373 recommends the method called melted salt method for the preparation of a support with a zirconia, alumina, silica or titanium oxide base, alone or mixed; the preferred support contains zirconia, alone or mixed with alumina, and is designed, after depositing the nickel and the molybdenum, to serve as a hydrotreating catalyst.

FR patent number 2,709,432 claims a catalyst that contains a support with a specific surface that is greater than or equal to 150 $m^2/g$, consisting of 60 to 99% by weight of zirconia and 1 to 40% by weight of oxide of at least one metal chosen from the group consisting of the metals of groups V, VI, VII, the noble metals such as ruthenium, osmium, rhodium, iridium, uranium, the phosphorous, arsenic and sulfur compounds. This support, essentially designed for hydrocarbon hydrotreating catalysts, is also prepared by the melted salts method.

In general, the catalysts proposed in the prior art as alternatives to the traditional catalysts on an alumina support have not proved to very satisfying because of their insufficient level of activity, meaning it is less than that of the traditional catalysts. Indeed, obtaining a high porosity of the support is done to the detriment of the additional activity brought by the metal oxide that is the alternative to the alumina. In other words, when we want to obtain a support that is sufficiently porous (which is indispensable to guarantee a good accessibility of the active sites to the molecules to be converted), we loose the specific catalytic properties that are the entire interest of theses metal oxides. This is why in general such catalysts are not currently used in industrial reactors.

SUMMARY OF THE INVENTION

In pursuing research in the field of catalysts with a zirconia base or other equivalent oxide base, the applicant has sought to act on the properties of these oxides. In doing so, it has been discovered that, surprisingly so, the zirconia or titanium oxide can become a material of choice that makes it possible to create excellent catalytic supports, provided its structure is of the crystalline type and is doped in an appropriate way with a small quantity of silica. Indeed it becomes possible to rigorously control all the characteristics of porosity without however losing the specific activity brought by these alternatives oxides. Thus the applicant has been able to develop industrial catalysts from a high porosity matrix, consisting essentially of metal oxides of the SVI group (of which zirconia and titanium oxide), where said catalysts have proved to have a level of activity that is greater when compared to the catalysts of the prior art.

Applicant has also discovered an original method of preparation that makes it possible to obtain such supports by controlling their porosity so as to obtain the desired active structures.

Thus, the applicant has developed a catalytic support that consists of a substantial quantity of at least one metal oxide of the SVI group from the Periodic Table of the Elements in which is incorporated silica, characterized by the fact that the mass ratio between the quantity of metal oxide of the SVI group and the quantity of silica it contains ranges between 5 and 70, that the metal oxide of the SVI group is in crystalline form and that the specific surface of the support is greater than or equal to 160 $m^2/g$.

Here and in what follows, the characteristics of porosity (specific surface, pore volume and average pore radius) are given in reference to the method of determination called B.E.T (Brunauer, Emmett, Teller) well known in the art.

The characteristics of structure and texture of the support as set forth in the invention have been optimized by acting on its method of manufacture, in particular by incorporating a small quantity of silica in the metal oxide of the SVI group, based on a determined mass ratio, and implementing the appropriate heat treatments, so as to precisely control the crystallinity of the SVI group metal oxide. The applicant has thus been able to control the properties of these oxides, which allowed her to select the most active formulas, the object of this invention.

Compared to the prior art, the support as set forth in the invention makes it possible to create more active catalysts that are more appropriate for use in an industrial reactor. Indeed, it has a high porosity that guarantees the accessibility of the active sites to the reactants while preserving the specific additional activity brought by the replacement of the alumina by a metal oxide of the SVI group. In other words, the catalysts developed from such supports have sites that are both more active and more accessible, which contributes to their excellent performances.

In addition, the properties of the support as set forth in the invention are stable at high temperatures. In particular its high porosity does not deteriorate either in the operational conditions of an industrial reactor or when subjected to a strong heat treatment, contrary to a good number of prior catalysts whose support is not essentially alumina. This stability is an undeniable advantage of the support as set forth in the invention. In particular, the catalysts manufactured from this support will be perfectly regenerative under traditional conditions of regeneration (for example, in the case of hydrocarbon treatment catalysts, by oxidation arranged at an increasing temperature, so as to provoke the progressive combustion of the coke deposited on the surface of the catalyst).

Furthermore, compared to the traditional alumina base catalytic supports, the support as set forth in the invention makes it possible to prepare catalysts that have an increased activity under similar reaction conditions. In particular, the results of nitrogen adsorption and desorption kinetics tests on this support show that the pores of the latter have a specific shape, probably similar to a cylindrical cavity, which increases the speed of entry and exit of the reactants in the pores compared to supports with an alumina base that have pores whose shape can be assimilated to that of a bottle of ink, meaning with a restriction of the entrance/exit section of the pores, causing a risk of congestion of the latter. This phenomenon helps explain the activity gain observed for the catalysts made from the support as set forth in the invention.

Lastly, these catalysts can be fully used in reactors of the traditional type where all that is needed is to substitute them, totally or partially, for the catalysts on an alumina support. This makes it possible, in a simple and inexpensive way, to considerably increase the performances of the procedures being considered, in particular the hydrocarbon upgrading procedures.

At the same time, the applicant has developed a method of preparation that makes it possible to control the structure and the texture of the catalytic supports with a metal oxide base of the SVI group and thus prepare a support as described above.

Lastly, the applicant used this support to prepare a certain number of catalysts conceived essentially for the treatment of hydrocarbons.

Therefore, the invention also relates to the method for preparing the support, as well as any catalyst prepared from this support. These aspects will be explained in more detail in the description and examples that follow.

In this invention, the catalytic support plays an essential role, to the extent that the greater activity of the hydrotreating catalysts obtained in the end, meaning after the active phases have been deposited, depends mostly on the intrinsic properties of the support. These properties must therefore be very carefully controlled.

The catalytic support as set forth in the invention contains a substantial quantity of at least one oxide of at least one metal of the SVI group, where said oxide must imperatively be present in crystalline form, meaning it must not be in the amorphous state. Preferably, the SVI group metal oxide is in a crystalline form of the tetragonal type. The determination of the crystalline structure of said metal oxide is performed, in a manner well-known in itself, by X-ray diffraction.

In addition, the texture of the support is controlled thanks to the incorporation, in said metal oxide of the SVI group, of a small quantity of silica, with a given weight ratio: the content of SVI group metal oxide by weight of the mixture ranges between 5 and 70 times its content in silica, which corresponds to a silica content that ranges between 1.5 and 16% by weight in a mixture that would only contain these two oxides. Preferably the mass ratio between the metal of the SVI group and the silica ranges between 8 and 30. By silica, we mean any silicon oxide.

Preferably the SVI group metal oxide that is contained in the support is chosen from among zirconia, titanium oxide or a mixture of these two oxides. Preferably, said SVI group metal oxide is zirconia. By zirconia, we mean zirconium dioxide.

Preferably, the specific surface of said support is greater than or equal to 180 $m^2/g$. Advantageously it has a pore volume that is greater than or equal to 0.25 cm³/g, preferably between 0.30 and 0.60 cm³/g included. Furthermore, its average pore radius is advantageously greater than or equal to 20 Å, preferably ranging between 20 and 120 Å included.

Essentially, the catalytic support as set forth in the invention contains the mixture described above, consisting of metal oxide of the SVI group (in particular zirconia, titanium oxide of a mixture of both) in crystallized form, doped with silica.

In addition it can contain a variable quantity of another refractory metal oxide usually used in the industry and that, as known, the man of the art may consider good to incorporate for various purposes, for example in order to obtain or strengthen certain properties, in order to facilitate the preparation or the shaping of the catalyst, or yet to reduce the costs of manufacturing the catalyst by replacing part of the support with raw materials that are less costly or more available than the metal oxides of the SVI group.

In particular, the support as set forth in the invention can advantageously contain a binding agent that has been incorporated in order to facilitate its shaping. Such a binder can consist of any refractory mineral oxide usually used for this reason, and in particular can be chosen from the group consisting of aluminas, silicas, silica-aluminas, alumino-silicates, clays and mixtures of these compounds. Preferably, said binder consists of alumina. Advantageously it can be incorporated in a quantity that ranges between 0.1 and 30% by weight in relation to the total weight of the support.

The catalytic support as set forth in the invention is an appropriate base for the manufacturing of all sorts of catalysts called supported, that is containing one or more compounds, deposited on said support, and playing the role of active phase. Very diverse compounds can thus be deposited on this support based on the type of activity that is sought, or in other words, the reaction to be catalyzed.

When the catalyst is meant to be used in a procedure for the treatment of hydrocarbon cuts, said active phase advantageously contains at least one metal or one compound of a metal of VIII group of the Periodic Table of the Elements. The metals or metallic compounds of this family are indeed particularly known for helping the reactions that involve transfers of hydrogen (which is often the case in reactions that take place in hydrocarbon upgrading).

According to a first method of execution, the active phase consists of one or more metals or metal compounds of group VIII of the Periodic Table of the Elements. Said metal of group VIII can for example be nickel, with a content ranging between 15 and 30% by weight in relation to the total weight of the catalyst. It can also, as a non restrictive example, be chosen from among platinum and palladium, and can be present at a content ranging between 0.1 and 2% by weight in relation to the total weight of the catalyst.

The catalysts as set forth in this first method of execution are particularly appropriate for a use in hydrocarbon hydrogenation reactions.

On the other hand, a metal or metallic compound of group VIII can be combined with one or more additional compounds, metallic or not, chosen for their specific activity in the reaction to be catalyzed.

Thus, according to a second method of execution, said active phase consists of one or more metals or metal compounds of group VIII of the Periodic Table of the Elements combined with at least one compound of the acid type. The metals of group VIII are then preferably chosen from among platinum, palladium, ruthenium, rhodium, osmium, iridium, and nickel. Platinum, alone or combined with palladium, is particularly preferred. These metals are advantageously present at a total content ranging between 0.1 and 2% by weight in relation to the total weight of the catalyst. The compound of the acid type can for example contain sulfate ions or tungstate ions whose content is variable based on the degree of acidity being sought.

The catalysts described according to this second method of execution are particularly appropriate for use in reactions that require the use of an acid or superacid type catalyst, such as in particular paraffin or olefin isomerization reactions, naphtenic hydrocarbon decyclization reactions, alkylation reactions, oligomerization reactions, hydrocarbon dehydration reactions, and oil cut hydrogenation reactions.

These catalysts are also particularly advantageous for deep hydrodearomatization reactions and/or desulphurization of oil cuts, of which gas oils in particular.

Lastly, these catalysts have proved to perform particularly well in procedures for the treatment of hydrocarbonic cuts that contain a substantial quantity of long chain paraffins (more than 7 atoms of carbon), whether linear or slightly branched, such as for example paraffins from a synthesis of the Fischer-Tropsch type (hydrocarbon synthesis from the mixture $CO+H_2$). The transformation of these paraffins by hydrocracking and/or hydroisomerization is often necessary in order to obtain either "large" products (gasolines, naphtha, middle distillates), or specialties (paraffins, sophisticated lubricants). The operational conditions must then be adjusted based on the reaction we wish to favor (hydrocracking or hydroisomerization), and the desired level of conversion. Advantageously, they can be the following: a temperature ranging between 20° C. and 400° C. (preferably between 150° C. and 300° C.), a pressure preferably ranging between $5.10^5$ and $200.10^5$ Pa, a hydrogen/hydrocarbon $H_2$/HC molecular ratio between 1 and 20 (preferably between 5 and 15).

According to a third method of execution, which is the preferred method of execution of the invention, the active phase consists of at least one metal or one compound of a metal of group VIII of the Periodic Table of the Elements. Advantageously these two types of metals are deposited on the support in the form of metal oxides, which are then transformed, totally or partially, into corresponding sulfides (metal sulfides) during an activation step that precedes the use of the catalyst.

Preferably, said group VIII is cobalt and/or nickel. The catalyst as set forth in the invention preferably consists of 2 to 10% by weight of the corresponding metal oxide.

Preferably, said SVI group metal is molybdenum and/or tungstene. The catalyst as set forth in the invention preferably consists of 10 to 25% by weight of corresponding metal oxide.

The catalysts as set forth in this third method of execution are particularly appropriate for use in hydrotreating procedures such as, in particular, procedures of hydrodesulphurization, hydrodenitrogenation, hydrostripping or hydrogenation of oil cuts such as gasolines, gas oils, vacuum distillates, long residues or vacuum residues.

The implementation conditions for these hydrotreating procedures will be optimized according to the type of hydrotreating planned, but also according to the nature of the charge to be treated and the treatment rate we wish to reach. The operational conditions of the hydrotreating procedures are not substantially modified in the presence of a catalyst as set forth in the invention, when compared with the usual conditions in the presence of a traditional catalyst on an alumina support. These conditions are usually the following:

a temperature ranging between 260 and 400° C., a total pressure ranging between 20 and 200.10$^5$ Pa (between 20 and 200 bars), a hydrogen/hydrocarbon volume ratio ranging between 50 and 2000 normal-to-liter/liter, an hourly volume velocity of the charge preferably ranging between 0.2 and 10 h$^{-1}$.

Although the catalysts described above are the preferred methods of execution of the invention, in no way should they limit[ ]its range. The man of the art can indeed create a large variety of supported catalysts from the catalytic support that is the object of the invention by depositing the appropriate active phases upon it.

The catalysts as set forth in the invention are of the solid type. They can come in all the forms to which the man of the art usually has recourse for the implementation of solid catalysts, and in particular in the form of particles such as beads, extrusions, pellets. They have an apparent filling density that usually ranges between 0.7 and 1.2 g/cm$^3$.

The method used for the preparation of the support as set forth in the invention must make it possible to rigorously control its structural and textural properties in order to obtain a support that meets the characteristics of the invention and makes an appropriate base for the preparation of highly active catalysts that meet the requirements of the industrial procedures.

The applicant has developed a preferred procedure for the preparation of such a catalytic support. This procedure consists essentially of the following steps:

a) from a solution of at least one salt, at least one metal of the SVI group, precipitation of the corresponding metal oxide(s), b) reflux ripening of the precipitate obtained, c) addition of silica d) ripening of the mixture, under agitation, e) washing, filtration then drying of the solid obtained, f) shaping of the solid, g) calcination of the solid.

Advantageously the precipitation step (a) of the SVI group metal oxide(s) can be performed by adding a basic solution to a solution (for example aqueous) in which are dissolved the appropriate metallic salts. The basic solution used can be any solution that makes it possible, by increasing the pH, to carry out the precipitation of a hydrated oxide from a solution of a precursor salt of said oxide. For example, it could be an ammonia solution or any other base known to the man of the art.

Salts of the SVI group metals likely to be used in order to obtain a precipitate of an SVI group metal oxide are well known to the man of the art. When we want to obtain a support with a zirconia base, we use a zirconium salt that may for example be chosen from the group made of nitrate, chloride, acetate, formate, zirconium or zirconyl oxalate, as well as zirconium alcoholates. When we want to obtain a support with a titanium oxide base, we use a titanium salt, which for example can be chosen from among the titanium chlorides or the titanium alcoholates.

The ripening step (b) is performed by bringing the solution in which the SVI group metal oxide gel is precipitated to a reflux for a sufficient period of time, advantageously between 1 and 50 hours and preferably between 12 and 36 hours.

As far as step (c) is concerned, silica is added to the SVI group metal oxide gel. This addition can take place in various ways, for example by a direct addition of silica, or by adding a solution of a silicon salt followed by an in situ precipitation. In the first case, we add a solution containing a colloidal silica gel to the SVI group metal oxide gel. In the second case, we add a silicon salt solution (such as ethyl orthosilicate or sodium silicate) to the SVI group metal oxide gel and we cause the silica precipitation by adding an acid.

The ripening step (d) is performed by keeping the mixture of silica gels and SVI group metal oxide under a strong agitation for a duration that advantageously ranges between 1 and 100 hours. This ripening can be under reflux or at room temperature. Preferably, when the SVI group metal oxide is titanium oxide, it takes place under reflux.

Step (e) corresponds to a filtration of the resulting suspension in order to recuperate the oxide gel. The latter is then washed and dried at moderate temperature (preferably around 100° C.), for example in an oven.

The solid shaping step (f) makes it possible to agglomerate the solid into a powder so as to form particles (for example beads, extrusions or pellets) in order to obtain a support that is qualified for the preparation of catalysts that can be used directly in an industrial reactor. In order to make this operation easier, it may be necessary to add a binder (alumina xerogels or any other industrial binder) to the power, then to mix this mixture before proceeding with the actual shaping by extrusion, "oil drop" method or any other method known for the shaping industrial catalysts.

The support thus obtained undergoes a calcination step (g) that must take place at a temperature that is sufficiently high, advantageously ranging between 550 and 850° C., for a duration that preferably ranges between 2 and 6 hours. This step is essential since it leads to the crystallization of the SVI group metal oxide. This calcination can advantageously take place under a controlled air flow.

The preparation of catalysts from the support as set forth in the invention is done in the traditional manner, by depositing at least one active phase on said support, according to methods that are well known to the man of the art. Of course, the method used will depend largely on the nature of the active phases to be deposited on the support.

For the deposit of metallic compounds, we can advantageously proceed by impregnation of the support using solutions of the metal compounds to be deposited, followed by a drying phase. For example, if we wish to deposit platinum on the support, we can proceed by impregnation using a solution of a platinum compound that can be chosen from the group consisting of chloroplatinic acid and complex platinum compounds.

When the active phase of the catalyst to be prepared consists of various compounds, they can, depending on their nature, be deposited either successively or simultaneously.

In particular, for the preparation of a catalyst that contains at least one metal (or metal compound) of group VIII combined with at least one metal (or metal compound) of the SVI group, it is preferable to deposit these various compounds simultaneously, through impregnation with a solution of a mixture of corresponding salts, followed by a drying phase.

Usually, such a deposit of an active phase is followed by a calcination step of the catalyst.

Furthermore, for some types of active phases it can be advantageous to proceed with the deposit before the completion of the preparation of the support and in particular before the calcination step g) of the support. This is the case for example for the active phases that consist of sulfides, tungstates or other similar compounds, whose grafting to the surface of the support is best when it is done before the first calcination (step g). For such active phases, it is therefore preferable to insert, in the sequence of preparation of the support, at least one step for the deposit of this active phase. Advantageously, said deposit step is inserted between steps e) and f), or between steps f) and g).

Lastly, before being able to use the catalyst in an industrial reactor, it is usually necessary to submit it to a final activation step (often completed in situ), for which the conditions, well known to the man of the art, depend essentially on the type of procedure being considered.

For example, in the hydrodesulphurization, hydrodenitrogenation and hydrostripping procedures, after having charged the catalyst in the reactor, we proceed with a previous activation step in situ, that consists in presulfurizing the active sites of the catalyst using known methods: in general, after putting the hydrogen under pressure between 50 and 200° C., we increase the temperature to approximately 300 to 400° C., making compounds likely to generate sulfur pass over the catalyst, such as hydrogen and hydrogen sulfide mixtures, thiols, disulfides or carbon sulfides or even a gas oil that contains sulfur.

The preparation methods described above are only suggestions for the execution of catalytic supports and catalysts according to the invention. Of course, they are not to be considered as limitations. Furthermore, the man of the art will be able, if necessary, to adapt the methods described through additional other well known operations, such as for example steps of solvent washing, drying, calcinations, and the incorporation of other usual refractory oxides.

The following examples are only designed to illustrate the invention and are in no way meant to have any limiting character.

EXAMPLES

Example 1

A. Preparation of Catalytic Support Samples as Set Forth in the Invention

Support S1

This test relates to the preparation of a catalytic support with a zirconia base in which is incorporated 4% by weight of silica.

We prepare a zirconium solution by dissolving 49.7 g of zirconyl nitrate $ZrO(NO_3)_2 6H_2O$ (Aldrich) in 497 ml of distilled water under agitation. We precipitate the zirconium hydroxide gel by adding 76 ml of an ammonia solution at 28% under strong agitation. The final pH is of 10. We let the gel ripen, still under agitation, for 48 hours under reflux. We cool it at room temperature. Its pH is then of 9.2 We add 20 ml of the ammonia solution at 28% under strong agitation to adjust the pH to 10.

We add 34.5 ml of water, under agitation, to 2.76 g of colloidal silica AS40 (Dupont de Nemours). This silica solution is poured over the zirconia gel and the mixture is left to ripen, under strong agitation, for two hours.

After filtration and washing to a pH of 7 (redispersal in 350 ml of water), the gel is dried overnight at 120° C. We obtain 21.58 g of solid.

The shaping is performed in an extruder syringe (diameter of 1 mm) after grinding and mixing the solid with 5.40 g of alumina xerogels of the Pural SB type (Condes) and 23.5 ml of distilled water. After drying overnight at 120° C., the extrusions are calcined at 640° C. for 4 hours. The quantity of support obtained is of approximately 20 g.

Support S2

This test relates to the preparation of a catalytic support with a zirconia base in which is incorporated 5% by weight of silica.

As with the support S1, we start with 49.7 g of $ZrO(NO_3)_2 6H_2O$. The zirconia gel is precipitated in the same way but the reflux only lasts 36 hours.

The gel is cooled at room temperature. The pH of the latter is then 9.3. We add 20 ml of ammonia solution at 28% under agitation to adjust the pH to 10.

We add 43 ml of water under agitation to 3.48 g of silica AS40. This silica is poured over the zirconia gel and the mixture is left to ripen under a strong agitation for 2 hours. After filtration and drying to pH 7 (redispersal in 350 ml water) the gel is dried overnight at 120° C. We obtain 21.91 g of solid.

The shaping is performed as for the support S1 but with 5.48 g of Pural SB alumina and 22.9 ml of water. The extrusions are also dried overnight at 120° C. and calcined for 4 hours at 640° C. The quantity of support obtained is of approximately 20 g.

Support S3

This test relates to the preparation of a catalytic support with a zirconia base in which is incorporated 7.5% by weight of silica.

As with the support S1, we start with 49.7 g of $ZrO(NO_3)_2 6H_2O$ and the zirconia gel is precipitated in the same way. The reflux lasts 36 hours. The gel's pH, at room temperature, is of 9.4 and we add 13 ml of ammonia solution at 28% to adjust it to 10.

We add 68 ml of water, under agitation, to 5.37 g of silica AS40, we then proceed in the same way as for the support S1. The quantity of recuperated matter, after drying, is of 22.75 g. The shaping is done in the same way as for the support S1 but with 5.69 g of Pural SB alumina and 23.9 ml of water. The extrusions are died overnight at 120° C. and calcined for 4 hours at 640° C. The quantity of support obtained is of approximately 20 g.

Support S4

This test relates to the preparation of a catalytic support with a titanium oxide base in which is incorporated 5% by weight of silica.

We prepare a solution of titanium by adding 180 ml of water under agitation to 231.4 g of a $TiCl_3$ solution (Prolabo) to 15% by weight in water. This solution is cooled in ice.

The titanium hydroxide gel is precipitated by adding, drop by drop, 150 ml of an ammonia solution at 28% under strong agitation. The final pH is of 10.

This gel is left to ripen, still under agitation, for 6 hours under reflux. It is left to cool at room temperature. Its pH is then of 9.7. We add 7 ml of an ammonia solution at 28% under agitation to adjust the pH to 10.

We add 30 ml of water under agitation to 2.37 g of silica AS40. This silica is poured over the titanium hydroxide gel under agitation and this gel is left to ripen still under a strong agitation for 24 hours under reflux. After filtration and drying until the chloride ions are completely eliminated (Negative $AgNO_3$ test); the gel is dried overnight at 120° C. We obtain 22.43 g of solid.

The shaping is performed in the same way as for the support S1 but with 5.86 g of Pural SB alumina and 21.7 ml of water. The extrusions are dried overnight at 120° C. and calcined for 4 hours at 575° C. The quantity of support obtained in this way is of approximately 20 g.

B. Properties of the Catalytic Support Samples

The following Table 1 shows the properties of the catalytic support samples obtained according to the methods of preparation listed above.

In these four samples, the SVI group metal oxide has a crystalline structure of the tetragonal type. In this example and in those that follow, the structure of the zirconia has been determined by x-ray diffraction.

The support S5 is a gamma alumina support of the traditional type. It corresponds to the catalytic supports traditionally used and is presented here as a typical reference of the prior art.

In the Table 1, S, Vp and Rp respectively designate the specific surface, the pore volume and the average pore radius of the catalyst.

In this example and those that follow, these characteristics have been determined using the method called B.E.T. (Brunauer, Emmett, Teller) by adsorption of nitrogen, such as it was described in the work by S. Lowell entitled "Powder Surface Area and Porosity", Society of Petroleum Engineers Advance Technology series (1984). More precisely, the specific surface and the pore volume have been determined by the B.E.T. method by adsorption of nitrogen using the ASAP 2400 device marketed by Micromeritics. The specific surface S is derived from the B.E.T. five point linear transform (with relative P/Po pressures=0.046; 0.08; 0.15; 0.25, and 0.33), the pore volume Vp is determined based on the quantity of nitrogen adsorbed at P/Po=0.985 and the average pore radius Rp is calculated using the formula Rp=2 Vp/S.

Before determining these characteristics, the sample was subjected to a primary vacuum degassing pretreatment at 250° C. for at least 8 hours.

The shape of the pores was derived from the nitrogen adsorption/desorption isotherms. For the support samples as set forth as in the invention (S1 to S4) the nitrogen adsorption and desorption kinetics are almost identical, whereas in the case of the alumina base support (S5), the desorption kinetic is distinctly less compared with that of the adsorption kinetic. In particular, this difference can be explained by the shape of the pores, similar to that of a cylindrical cavity, in the first case, and that of a bottle of ink in the second case.

a) Preparation of Impregnation Solutions

Molybdenum solution:
dissolution of 3.10 g of ammonia heptamolydate in an aqueous solution consisting of 7 to 14 $cm^3$ of distilled water and 2.1 g of diamine ethylene.

Cobalt Solution:
dissolution of 1.95 g of cobalt nitrate in 7 to 14 $cm^3$ of distilled water.

These solutions are used for the impregnation of 20 $cm^3$ of support and are always used immediately after their preparation. The volume of water used was adjusted based on the porosity of the support to impregnate. For the samples presented here, this volume always ranged between 7 and 14 $cm^3$.

b) Impregnation of the Catalytic Support Samples

The impregnation of the support previously dried in an oven at 120° C. is performed in a flask animated by a rotary movement and under a permanent flow of nitrogen. The addition of the molybdenum solution on the support in motion is guaranteed by a pump with a constant flow of 30 $cm^3$/hour. After this operation, the impregnated support is maintained in the flask for one hour, but with a slower rotation velocity. This support is then dried for two hours in an oven at 120° C. before being placed once again in the rotating flask for the impregnation with the cobalt solution that is performed in the same way as for the molybdenum.

c) Drying and Calcination of the Catalyst Samples

Following a drying period of 16 hours in an oven at 120° C., each sample is calcined at a temperature of 500° C. under a controlled air flow (50 liters/hour). The velocity at which the temperature rises is 1.2° C./minute and the plateau at 500° C. is maintained for a period of 4 hours.

Table III below illustrates the characteristics of the catalyst samples obtained in this way.

TABLE I

| Support | SVI gr. oxide/silica (mass ratio) | S ($m^2/g$) | $V_p$ ($cm^3/g$) | $R_p$ ($10^{-10}$ m) | Crystallinity | Shape of the pores |
|---|---|---|---|---|---|---|
| S1 | 24 | 199 | 0.34 | 37 | Tetragonal | Cylindrical Cavity |
| S2 | 19 | 203 | 0.36 | 37 | Tetragonal | Cylindrical Cavity |
| S3 | 12 | 199 | 0.37 | 37 | Tetragonal | Cylindrical Cavity |
| S4 | 19 | 211 | 0.38 | 32 | Tetragonal | Cylindrical Cavity |
| S5 | / | 271 | 0.75 | 39 | Gamma | "Ink bottle" |

C. Preparation of Catalyst Samples

Supports S1 through S5 described above were used in order to prepare hydrocarbon hydrotreating catalyst samples by depositing an SVI group metal (molybdenum), in the form of an oxide, on their surface, and a group VIII metal (cobalt) in the form of an oxide.

Catalyst samples C1 through C5, prepared respectively from supports S1 through S5, all have the following composition, illustrated in Table II

TABLE II

| Quantity of support | 81.5% by weight |
|---|---|
| $MoO_3$ content | 15.4% by weight |
| CoO content | 3.1% by weight |

These catalyst samples have been prepared in the following manner:

TABLE III

| Catalyst | S ($m^2/g$) | $V_p$ ($cm^3/g$) | $R_p$ ($10^{-10}$ m) |
|---|---|---|---|
| C1 | 171 | 0.31 | 34 |
| C2 | 162 | 0.30 | 35 |
| C3 | 158 | 0.30 | 37 |
| C4 | 155 | 0.30 | 30 |
| C5 | 238 | 0.55 | 37 |

D) Activity of the Catalyst Samples

The activity of samples C1 through C5 was determined in the hydrodesulphurization procedure of an oil cut of the gas oil type. The tests were performed in a pilot reactor, under conditions that were identical to those of the industrial procedures.

a) Charging and Activation of the Catalyst

For each test, 20 cm$^3$ of the catalyst sample involved were diluted in 47 cm$^3$ of silicon carbide and the whole thing was charged in the reactor. The catalyst was then activated in situ, through presulphurization of the cobalt and molybdenum oxides present at its surface, by making a presulphurization charge consisting of straight run gas oil at 1.4% by weight of sulfur additivated at 1% by weight of dimethyldisulfide pass over the catalyst under the following conditions:

| | |
|---|---|
| temperature: | 360° C. |
| total pressure: | 30.10$^5$ Pa |
| vvh (charge volume per unit of catalyst volume and per hour): | 3.0 h$^{-1}$ |
| hydrogen/hydrocarbon ratio (H$_2$/HC): | 150 Nl/l(normal-to-liters/titer) | b) Conditions of the Test

The catalyst samples activated in this manner were used to desulfurize a hydrocarbon charge that is a classic oil cut, comprised of an isovolumic mixture of straight run gas oil (50% by volume) and I.C.O. (from "Light Cycle Oil"), a gas oil produced by a catalytic cracking procedure (50% by volume). This charge contains 1.72% by weight of sulfur.

The operational conditions retained to test the catalyst samples are the following:

| | |
|---|---|
| total pressure: | 30.10$^5$ Pa |
| hourly space velocity (v.v.h.): | 3.0 h$^{-1}$ |
| H$_2$/HC ratio: | 150 Nl/l |

Each time, the catalyst sample was subjected to a first step of stabilization for a minimum of 24 hours, during which the charge is passed over the catalyst under the operational conditions of the test, at a temperature of 360° C.

Following this stabilization step, we proceed with the actual test by analyzing the effluents that emanate from the pilot at various reaction temperatures (three temperatures were tested: 340° C.; 360° C.; 380° C.)

c) Activity of the Catalyst Samples

Table IV below illustrates the results of the desulphurization tests.

TABLE IV

| | | Sulfur content of effluents (% by weight) | | |
|---|---|---|---|---|
| Catalyst | Charging density (g/cm$^3$) | At 340° C. | At 360° C. | At 380° C. |
| C1 | 0.96 | 0.188 | 0.075 | 0.031 |
| C2 | 0.95 | 0.175 | 0.067 | 0.028 |
| C3 | 0.97 | 0.184 | 0.101 | 0.034 |
| C4 | 0.81 | 0.215 | 0.092 | 0.045 |
| C5 | 0.75 | 0.218 | 0.122 | 0.055 |

The above results show that the catalysts that comply with the invention (namely the catalysts C1, C2, C3, C4) make it possible to obtain effluents whose sulfur content is clearly less than that obtained with the catalyst C5, which is a traditional alumina base catalyst.

In other words, under the conditions of the test, which correspond to the traditional hydrodesulphurization conditions in an industrial reactor, the catalysts developed from the support as set forth in the invention have an excellent activity since they make it possible to desulfurize the charge in a more thorough manner that the traditional catalysts.

Table V below allows us to compare in more detail the performances of the catalyst samples as set forth in the invention (C1 through C4) with the performances of the traditional catalyst (C5). This table corresponds to the results obtained for the desulphurization tests carried out at a temperature of 360° C.

TABLE V

| Catalyst | Desulphurization Rate of the charge (% by weight) | ΔT (in ° C.) | RVA |
|---|---|---|---|
| C1 | 95.6% | −13 | 142 |
| C2 | 96.1% | −15 | 154 |
| C3 | 94.1% | −6 | 115 |
| C4 | 94.6% | −8 | 123 |
| C5 | 92.9% | 0 | 100 |

The ΔT parameter, calculated for the catalysts C1 through C4 using the traditional catalyst C5 as a reference, corresponds to the increase in temperature that would take place with these catalysts C1 through C4, when functioning at an identical desulphurization rate.

The RVA parameter, (from "Relative Volume Activity") makes it possible to compare the activities of the catalyst samples, for an equal sample volume, with the activity of the reference sample C5.

$$RVA = \frac{(So/S1)^{n-1} \text{ sample} - 1}{(So/S1)^{n-1} \text{ reference} - 1}$$

where:

$So$ = initial sulfur rate (by weight)

$S1$ = sulfur rate of the effluents (by weight)

$n$ = order of the reaction = 1.6

The above results show the increased performances of the catalysts as set forth in the invention.

On the one hand, under identical operational conditions, they allow for a more complete desulphurization of the charge.

On the other hand, the gain in activity brought by the catalysts can be used in order to operate under softer conditions. Indeed, the ΔT parameter shows that the catalysts as set forth in the invention (C1 through C4) make it possible to obtain a same desulphurization rate while operating at a lower temperature than the traditional catalysts (C5). The advantages tied to a more even reaction temperature are well known to the man of the art; in particular, on the one hand a reaction temperature that is too high is incompatible with the restrictions tied to the metallurgy of the reactor and, on the other hand, it might prematurely deactivate the catalyst by depositing coke on its surface.

Lastly, the RVA parameter shows that in order to obtain an identical desulphurization rate, the quantity of catalyst to be used is less significant if we use a catalyst as set forth in the invention than if we use a traditional catalyst.

We see from the above-mentioned examples that the supports as set forth in this invention make it possible to develop excellent hydrotreating catalysts that can advantageously replace the traditional catalysts in the industrial procedures.

Example 2

This example illustrates the preparation of an acid type catalyst by depositing an active phase consisting of a Periodic Table of the Elements group VIII metal combined with tungstate ions on a support as set forth in the invention.

A. Preparation and Characterization of the Support

We prepare a zirconium solution by dissolving 52.5 g of zirconyl nitrate $ZrO(NO_3)_2,6H_2O$ (Aldrich) in 525 ml of distilled water. The solution is agitated under heat to complete the dissolution of the salt, it is then cooled at room temperature. We then precipitate the zirconium hydroxide gel by adding 80 ml of an ammonia solution at 28%, under agitation. The gel is left to ripen, still under agitation, for 36 hours under reflux. It is cooled at room temperature and 17 ml of the ammonia solution at 28% is added under strong agitation to adjust the pH to 10.

We add 45 ml of water, under agitation, to 3.6 g of colloidal silica AS40 (Dupont de Nemours). We then mix this silica solution with the zirconia gel solution by adding 10 ml of the ammonia solution at 28% so as to maintain a pH of 10. The mixture is left to ripen for 36 hours under reflux and under agitation. After filtration and washing to a pH of 7, the gel is dried at 120° C.

A sample of this gel is taken and calcined for 3 hours at 750° C. so as to be able, after cooling, to characterize the support sample prepared in this way. This sample has the following characteristics:

Zirconia/silica mass ratio: 19,
Specific surface: 210 m²/g,
Volume of the pores: 0.47 cm³/g,
Structure of the zirconia: crystalline structure of the tetragonal type B. Preparation and Characterization of the Catalyst 24.3 g of dried zirconia-silica gel are mixed with a solution of 150 ml of distilled water in which are dissolved 5.4 g of ammonia metatungstate. The solvent is evaporated in a rotating evaporator, and the solid obtained is dried overnight at 120° C.

The shaping is then performed in an extruding syringe (diameter of 1 mm) after grinding and mixing 23.25 g of the solid with 5.81 g of alumina xerogels of the Pural SB type (Condea) and 22 ml of distilled water. After drying overnight at 120° C. the extrusions are calcined at 750° C. for 3 hours.

The platinum is then deposited so as to obtain a platinum content of 0.5% by weight in relation to the total weight of the catalyst. This deposit is performed in a traditional manner by impregnation, meaning by putting the extrusions in contact with an aqueous solution of $Pt(NH_3)_4Cl_2H_2O$. After evaporation of the aqueous phase using a rotary evapator, the solid is dried overnight at 120° C. and lastly it is calcined for 4 hours at 480° C.

The catalyst obtained in this way has a specific surface of 179 m²/g and a pore volume of 0.41 cm³/g.

C. Activity of the Catalyst

The activity of the catalyst has been studied in a hydroconversion reaction of long paraffins in a pilot reactor and under conditions similar to those of the industrial procedures.

10 g of catalyst were placed in the reactor, the catalyst was then activated in situ, by reduction under a hydrogen flow of 6l/h at atmospheric pressure and a temperature of 300° C. 16 hours.

The catalyst that is activated in this way was used to isomerize a hydrocarbon charge consisting at 100% of normal-dodecane. The latter was dried to the fullest on zeolite 3A before being mixed with hydrogen and put in contact with the catalyst.

The operational conditions are the following:

| total pressure: | $30.10^5$ Pa, |
|---|---|
| hourly space velocity by weight (p.p.h.): | $1.0\ h^{-1}$ |
| $H_2$/HC molar ratio: | 3 |

Several tests were carried out at various temperatures. The results obtained are shown in Table VI below:

TABLE VI

| Temperature (° C.) | Conversion (%) | Yield i-C12(%) | Yield C5–C11(%) | Selectivity i-C12(%) | Selectivity C5–C11(%) | Selectivity C1–C4(%) |
|---|---|---|---|---|---|---|
| 210 | 28.5 | 25.1 | 0.9 | 87.9 | 3.1 | 9.0 |
| 220 | 43.1 | 35.9 | 3.1 | 83.3 | 7.3 | 9.4 |
| 230 | 62.4 | 36.8 | 15.8 | 59.0 | 25.3 | 15.7 |
| 240 | 78.5 | 28.7 | 35.2 | 36.6 | 44.8 | 18.6 |
| 250 | 97.3 | 12.3 | 73.1 | 12.6 | 75.1 | 12.3 |

As shown in the above table, the conversion is substantial as of 210° C. which indicates a good activity from the catalyst.

Essentially, two reactions take place:

hydroisomerization of the normal-dodecane into iso-dodecane (n-C12→iC12)

hydrocracking of the normal-dodecane into lighter hydrocarbons, each time with an excellent selectivity in the favor of intermediary hydrocarbons containing from 5 to 11 atoms of carbon; it essentially relates to branched heptanes and octanes (C7 and C8) that are sought products because they are easily amenable to beneficiation.

The above results show that at temperatures of less than 230° C., the catalyst as set forth in the invention makes it possible to hydroisomerize the normal-dodecane into iso-dodecane with an excellent selectivity (greater than 80%). At higher temperatures, the selectivity of this reaction decreases to the benefit of the hydrocracking reactions. The catalyst as set forth in the invention then has an excellent activity for the cracking of the normal-dodecane, with a very good selectivity to the benefit of intermediary hydrocarbons (C5 through C11) that are amenable to beneficiation. Conversely, the formation of light hydrocarbons (C1 through C4), not often sought, remains very limited.

Example 3

This example below illustrates the preparation of a catalyst of the acid type by depositing an active phase consisting of two Periodic Table of the Elements group VIII metals combined with tungstate ions on a support as set forth in the invention.

A. Preparation and Characterization of the Catalyst

We prepare a supported catalyst according to the method described in Example 2. The only difference relates to the final step of the deposit of the group VIII metal: in addition to the platinum, we deposit palladium, also by impregnation. These two metals are deposited in such a manner that the catalyst has a final content of 0.7% by weight of each of the two metals (0.7% of Pt and 0.7% of Pd)

Immediately prior to depositing the tungstate ions, a sample of the zirconia-silica gel was taken and calcined for 3 hours at 750° C., so that, after cooling, the sample of the support prepared in this way can be characterized. This sample has the following characteristics:

zirconia/silica mass ratio: 19 specific surface: 222 m$^2$/g volume of the pores: 0.41 cm$^3$/g average pore radius: 37.10$^{-10}$ m structure of the zirconia: crystalline structure of the tetragonal type A. Activity of the Catalyst The activity of the catalyst was studied in a hydrodearomatization reaction of a hydrocarbon cut rich in heavy aromatic compounds, in a pilot reactor under conditions that are similar to those of the industrial procedures. 20 ml of the catalyst were placed in the reactor, the catalyst was then activated in situ in the following way: calcination under a flow of dry air at 440° C. for 4 hours, cooling at room temperature, purging with nitrogen, then reduction under hydrogen flow at 300° C. for 8 hours.

The catalyst activated in this way was used to hydrogenate a charge of hydrocarbons consisting of 90.4% by weight of normal-dodecane and 9.6% by weight of 2-methyl-naphtalene (where the hydrocarbon contains two aromatic rings).

The charge is dried to the fullest over a molecular sieve (3A) before being mixed with hydrogen and put in contact with the catalyst.

The operational conditions are the following:

| | |
|---|---|
| total pressure: | 50.10$^5$ Pa, |
| temperature at the entrance of the reactor: | 235° C. |
| hourly space velocity by volume (v.v.h.) | 1 h$^{-1}$ |
| mass ratio H$_2$/HC: | 500 Nl/l |

Table VII below shows the results of this test, in terms of composition (% by weight) of the initial charge and the effluents:

TABLE VII

| | Charge | Effluents |
|---|---|---|
| Content of non cyclical saturated hydrocarbons | 90.4 | 96.1 |
| Content of Bicyclical hydrocarbons of which: | 9.6 | 3.9 |
| aromatic, of which: | 9.6 | 2.1 |
| * 2–methyl-naphtalene | 9.6 | 0 |
| * methyl-tetraline | 0 | 2.1 |
| saturated (methyl-decaline) | 0 | 1.8 |

The above results illustrate the excellent performances of the catalyst as set forth in the invention for the hydrodearomatization of oil cuts. Indeed, the 2-methyl-naphtalene is completely converted.

Essentially two types of reactions take place:

hydrogenation of the 2-methyl-nephtalene into methyltetraline (one single aromatic ring) and methyl-decaline (no aromatic ring) with a conversion rate of 100% opening of the cyclical hydrocarbons that result from the hydrogenation of the 2-methyl-nephtaline, with a conversion rate of 59.4%.

We must note that parallel to these hydrodearomatization reactions, a substantial part of the normal-dodecane is hydro-isomerized into iso-dodecane, or hydrocracked into branched intermediary paraffins that consist of 5 to 11 atoms of carbon.

The formation of undesirable light hydrocarbons (1 to 4 atoms of carbon) remains very minor (1.8% by weight in the effluents).

Therefore, the catalyst in Example 3 has an excellent activity for the hydrodearomatization of hydrocarbon cuts since it not only makes it possible to hydrogenate but also to decyclicize, the aromatic compounds that are present while limiting the phenomena of cracking in undesirable light hydrocarbons. For example, it proves to be particularly interesting for hydrotreating procedures of gas oils cuts, in which it not only has the effect of reducing the content of undesirable aromatic compounds and increasing the cetin number but also of improving the flow properties without heat (thanks to the isomerization of the normal-paraffins into iso-paraffins).

In conclusion, without being restrictive, Examples 1 through 3 above illustrate the variety of catalysts likely to be prepared from the support as set forth in the invention by depositing one or more active phases adapted to the reaction we wish to catalyze on this support. They also illustrate the excellent degree of activity of the catalysts that are likely to be prepared from this support.

What is claimed is:

1. Catalytic support comprising a quantity of at least one metal oxide selected from the group consisting of zirconia, titanium oxide, and a mixture thereof, in which is incorporated silica, wherein the mass ratio between the quantity of the metal oxide and the quantity of silica it contains ranges between 5 and 70, the metal oxide is in crystalline form, and the specific surface of the support is greater than or equal to 160 m$^2$/g, wherein the support has a pore volume greater than or equal to 0.25 cm$^3$/g and less than or equal to 0.60 cm$^3$/g.

2. Catalytic support as set forth in claim 1, wherein the mass ratio between the metal oxide and the silica ranges between 8 and 30.

3. Catalytic support as set forth in claim 1, wherein the metal oxide is zirconia.

4. Catalytic support as set forth in claim 1, wherein the metal oxide is in a crystalline form of tetragonal type.

5. Catalytic support as set forth in claim 1, said specific surface is greater than or equal to 180 m$^2$/g.

6. Catalytic support as set forth in claim 1, having a pore volume ranging between 0.30 and 0.60 cm$^3$/g inclusive.

7. Catalytic support as set forth in claim 1, having an average pore radius greater than a equal to 20 Å.

8. Catalytic support as set forth in claim 1, also containing a variable quantity of another refractory metal oxide selected from the group consisting of aluminas, silicas, silicaaluminas, alumino-silicates, clays and mixtures thereof.

9. Catalytic support as set forth in claim 1, containing a binding agent that includes a refractory mineral oxide selected from the group consisting of the aluminas, the silicas, the silica-aluminas, the alumino-silicates, the clays and the mixtures of these compounds.

10. Supported catalyst containing one or more metals or one or more compounds that make up the active phase, deposited on a support as set forth in claim 1.

11. Catalyst as set forth in claim 10, wherein said active phase comprises at least one metal or one metal compound of group VIII of the Periodic Table of the Elements, possibly combined with one or more additional compounds, metallic or not, chosen for their specific activity in the reaction to be catalyzed.

12. Catalyst as set forth in claim 10, wherein said active phase comprises one or more metals or metal compounds of group VIII of the Periodic Table of the Elements.

13. Catalyst as set forth in claim 10, wherein said active phase comprises of one or more metals or metal compounds of group VIII of the Periodic Table of the Elements, combined with at least one acid type compound.

14. Catalyst as set forth in claim 13, wherein the metals of Group VIII are selected from the group consisting of platinum, palladium, ruthenium, rhodium, osmium, iridium, and nickel and the acid type compound is selected from the group consisting of sulfide ions and tungstate ions.

15. Catalyst as set forth in claim 10, wherein the active phase contains at least one metal or metal compound of group VIII of the Periodic Table of the Elements and at least one metal or metal compound of molybdenum and/or tungsten.

16. Catalyst as set forth in claim 15, wherein the metal of group VIII is cobalt and/or nickel and the catalyst includes 2 to 10% by weight of the corresponding metal oxide.

17. Catalyst as set forth in claim 15, wherein the catalyst contains between 10 and 25% by weight of the metal oxide of molybdenum and/or tungsten.

18. Catalyst as set forth in claim 15, wherein the two types of metals are deposited on the support in the form of metal oxides which are then transformed, totally or partially, into corresponding sulfides (metal sulfides) during an activation step that precedes the use of the catalyst.

19. Procedure for the preparation of a catalyst support, comprising the following steps:
   (a) from a solution of at least one salt of at least one of zirconium and titanium, precipitating the corresponding metal oxide(s);
   (b) ripening under reflux the precipitate obtained;
   (c) adding silica;
   (d) ripening the mixture, under agitation;
   (e) washing, filtering and then drying the solid obtained from step (d);
   (f) shaping the solid; and
   (g) calcining the solid to thereby obtain a catalytic support comprising a quantity of at least one metal oxide selected from the group consisting of zirconia, titanium oxide, and a mixture thereof, in which is incorporated silica, wherein the mass ratio between the quantity of the metal oxide and the quantity of silica it contains ranges between 5 and 70 the metal oxide is in crystalline form, and the specific surface of the support is greater than or equal to 160 $m^2/q$, wherein the support has a pore volume greater than or equal to 0.25 $cm^3/q$ and less than or equal to 0.60 $cm^3/g$.

20. Procedure as set forth in claim 19, wherein the precipitation step (a) is performed by adding a basic solution to said solution of at least one salt of at least one of zirconium and titanium.

21. Procedure as set forth in claim 19, wherein the ripening step (b) is performed by bringing the solution to a reflux in which is precipitated at least one of zirconia and titanium oxide gel for a period of time ranging between 1 and 50 hours.

22. Procedure as set forth in claim 19, wherein the ripening step (d) is performed by maintaining a strong agitation of the mixture of silica and at least one of zirconia and titanium oxide gels for a period of time that ranges between 1 and 100 hours.

23. Procedure as set forth in claim 19, wherein the calcination step (g) takes place at a temperature ranging between 550 and 850° C. for a period of time that ranges between 2 and 6 hours.

24. Procedure for preparing a catalyst, comprising the deposit of at least one active phase on a support prepared according to claim 19, where said deposit is performed before and/or after the full completion of the preparation of the support.

25. Procedure as set forth in claim 24, wherein between steps e) and f), or between steps f) and g) of the sequence of the support preparation, a step of active phase deposit is introduced.

26. A method of using the catalyst set forth in claim 10, comprising employing the catalyst in a procedure for the treatment of hydrocarbon cuts.

27. A method of using the catalyst set forth in claim 12, comprising employing the catalyst in a hydrocarbon hydrogenation reaction.

28. A method of using the catalyst set forth in claim 13, comprising employing the catalyst in a reaction that requires the use of an acid or superacid catalyst.

29. A method of using the catalyst set forth in claim 13, comprising employing the catalyst in hydrodearomatization and/or oil cut deep desulphurization reactions.

30. A method of using the catalyst set forth in claim 13, comprising employing the catalyst in a long paraffin hydrocracking and/or hydroisomerization reaction, at more than 7 atoms of carbon.

31. A method of using the catalyst set forth in claim 15, comprising employing the catalyst in a hydrotreating procedure.

32. Catalytic support as set forth in claim 7, having an average pore radius between 20 and 120 Å inclusive.

33. Procedure as set forth in claim 21, wherein the period of time ranges between 12 and 36 hours.

34. A method of using a catalyst as set forth in claim 28, wherein the reaction that requires the use of an acid or superacid catalyst is selected from the group consisting of paraffin or olefin isomerization reactions, naphthenic hydrocarbon decyclization reactions, alkylation reactions, oligomerization reactions, hydrocarbon dehydration reactions, and oil cut hydrogenation reactions.

35. A method of using a catalyst as set forth in claim 29, wherein the oil cut is gas oils.

36. A method of using a catalyst as set forth in claim 31, wherein the hydrotreating procedure is selected from the group consisting of hydrodesulphurization, hydrodenitrogenation, hydrostripping and hydrogenation procedures of oil cuts.

37. A method of using a catalyst as set forth in claim 36, wherein the oil cuts are selected from the group consisting of gasolines, gas oils, vacuum distillates, atmospheric residues and vacuum residues.

* * * * *